(12) United States Patent
Marini

(10) Patent No.: US 12,721,746 B1
(45) Date of Patent: Sep. 1, 2026

(54) SNORE PREVENTION CLIP

(71) Applicant: Samuel P. Marini, Naples, FL (US)

(72) Inventor: Samuel P. Marini, Naples, FL (US)

(*) Notice: Subject to any disclaimer, the term of this patent is extended or adjusted under 35 U.S.C. 154(b) by 0 days.

(21) Appl. No.: 19/442,107

(22) Filed: Jan. 7, 2026

Related U.S. Application Data

(60) Provisional application No. 63/750,983, filed on Jan. 29, 2025.

(51) Int. Cl.
*A61F 5/56* (2006.01)

(52) U.S. Cl.
CPC .................................... *A61F 5/566* (2013.01)

(58) Field of Classification Search
CPC .... A61F 5/05; A61F 5/56; A61F 5/566; A61F 2005/563; A61C 7/08; A61C 7/36
See application file for complete search history.

(56) References Cited

U.S. PATENT DOCUMENTS

D924,398 S 7/2021 Pellissard et al.
2018/0200103 A1 7/2018 Keropian
2024/0390179 A1* 11/2024 Miao ........................ A61F 5/05

FOREIGN PATENT DOCUMENTS

DE 19933356 A1 2/2001
JP 2001161736 A 6/2001
JP 7083077 B2 6/2022

* cited by examiner

*Primary Examiner* — Daniel A Miller
(74) *Attorney, Agent, or Firm* — John Rizvi; John Rizvi, P.A.—The Patent Professor®

(57) ABSTRACT

A snore prevention clip includes a top teeth engaging portion, a bottom teeth engaging portion and a connecting portion. The snore prevention clip provides a minimally obstructive clip that attaches to the teeth of a wearer with the majority of the snore prevention clip being held outside the mouth of the wearer. The top teeth engaging portion and the bottom teeth engaging portion are in a staggered configuration to enable comfortable forward movement of the lower jaw, keeping the airway of a wearer open and thereby preventing snoring.

15 Claims, 6 Drawing Sheets

SNORE PREVENTION CLIP

CROSS-REFERENCE TO RELATED APPLICATIONS

This application claims the benefit of U.S. Provisional Patent Application Ser. No. 63/750,983, filed on Jan. 29, 2025, which is incorporated by reference herein in its entirety.

FIELD OF THE INVENTION

The present invention generally relates to the field of medical devices and more specifically relates to a device for preventing snoring.

BACKGROUND OF THE INVENTION

Snoring is a common issue that affects millions of people worldwide, disrupting sleep for both the person snoring and their bed partners. It occurs when airflow is partially obstructed during sleep, causing tissues in the throat to vibrate. This vibration produces the distinctive snoring sound, which can range from mild to severe.

The primary cause of snoring lies in the relaxation of the throat and tongue muscles during sleep. When these muscles relax excessively, the airway narrows, causing turbulence as air moves through. This turbulence creates vibrations in the soft tissues of the throat, including the uvula and soft palate, leading to snoring.

One effective way to reduce snoring is by addressing the position of the jaw during sleep. The jaw plays a crucial role in maintaining an open airway, and its position can significantly impact airflow. When the jaw is positioned too far back, it can cause the tongue and soft tissues to collapse toward the back of the throat, further obstructing the airway. This obstruction increases the likelihood of snoring and may even lead to more serious breathing difficulties during sleep.

Bringing the jaw forward can help alleviate snoring by creating more space in the airway. This forward position moves the base of the tongue and associated soft tissues away from the back of the throat, reducing the potential for obstruction.

By widening the airway, airflow becomes smoother, minimizing the vibrations that cause snoring. This approach is particularly beneficial for individuals whose snoring is linked to jaw positioning or anatomical factors affecting the throat Several devices are available to address snoring, ranging from simple nasal strips to more advanced solutions for individuals with specific anatomical concerns.

One widely recommended option is the mandibular advancement device (MAD), commonly referred to as a mouth guard for snoring. This device is designed to reposition the jaw forward during sleep, helping to keep the airway open and reduce the vibrations in the throat that cause snoring. In particular. the mouth guard works by advancing the lower jaw, which pulls the tongue and soft tissues forward as well. This increased airway space reduces the likelihood of blockages and ensures smoother airflow during sleep.

However, mandibular advancement devices (MADs) are not without their drawbacks. One of the main issues is that these devices are held entirely within the mouth, which can make them feel intrusive or uncomfortable, especially for first-time users. For some, the sensation of having a foreign object in their mouth during sleep can cause excessive salivation, gagging, or even difficulty falling asleep. Over time, these issues may subside as users adjust, but they can pose a barrier for those with sensitive mouths or a strong aversion to oral appliances.

Another common problem with MADs is their tendency to dislodge during sleep. As users move or shift positions, the device may slip out of place, rendering it ineffective. This is particularly true for individuals who grind their teeth or clench their jaw at night, as these habits can loosen the device's fit.

Once dislodged, the device no longer maintains the forward position of the jaw, allowing the airway to narrow again and causing snoring to resume. This can frustrate users and reduce the overall efficacy of the device over time.

Additionally, custom MADs often require detailed impressions or casts of the mouth to ensure a proper fit. While this level of customization enhances comfort and effectiveness, the process can be time-consuming and expensive. Patients must typically visit a dentist or orthodontist to have molds taken, which can be an inconvenience. Furthermore, any significant dental changes, such as tooth loss or orthodontic work, may necessitate creating a new device, adding to the cost and effort involved.

In addition, despite the importance in the lower jaw being moved forward to prevent snoring, a significant limitation with many mandibular advancement devices (MADs) arises from the way they are designed. When molds or impressions are taken for these devices, they are typically based on the teeth in their normal, resting position rather than the forward-jawed position required for the device to function optimally.

This discrepancy can create challenges for users. When the jaw is moved forward during sleep, the device may not fit as securely as it should because the mold does not account for the shifted alignment of the teeth and jaw. This misfit can lead to discomfort, reduced stability, or even the device slipping out of place during the night.

Additionally, a poor fit compromises the effectiveness of the device, as it may not adequately maintain the jaw in the forward position needed to keep the airway open. For users, this mismatch between the molded design and the functional positioning of the jaw can result in frustration and diminished results.

Accordingly, a suitable solution is desired.

SUMMARY OF THE INVENTION

The present invention is directed to a snore prevention clip. The snore prevention clip advantageously addresses the aforementioned deficiencies by providing a minimally obstructive clip that attaches to the teeth of a wearer with the majority of the snore prevention clip being held outside the mouth of the wearer. Thus, the aforementioned problems associated with current devices in the prior art, such as mandibular advancement devices (MADs), are avoided.

In a first implementation of the invention, a snore prevention clip may comprise a top teeth engaging portion, a bottom teeth engaging portion and a connecting portion at which the top teeth engaging portion and the bottom teeth engaging portion are joined.

In a second aspect, the snore prevention clip staggers the positioning of the upper and lower teeth, bringing the lower jaw forward to maintain an open airway and prevent snoring.

In another aspect, the snore prevention clip provides a simple, painless design to prevent snoring in wearers.

In another aspect, the snore prevention clip is attached primarily outside of the mouth instead of inside the mouth like current devices in the prior art.

In another aspect, the top teeth engaging portion, the bottom teeth engaging portion and the connecting portion may be formed as one unitary piece.

In another aspect, the snore prevention clip may include a snore prevention clip first end, a snore prevention clip second end opposite the snore prevention clip first end, a snore prevention length between the snore prevention clip first end and the snore prevention clip second end, a snore prevention clip top, a snore prevention clip bottom opposite the snore prevention clip top, a snore prevention clip left side and a snore prevention clip right side opposite the snore prevention clip left side.

In another aspect, the top teeth engaging portion and the bottom teeth engaging portion may be formed as a pair of flexible jaws joined together and able to move relative to the connecting portion.

In another aspect, the top teeth engaging portion may include a top teeth portion first end, a top teeth portion second end opposite the top teeth portion first end, a top teeth portion length between the top teeth portion first end and the top teeth portion second end, a top teeth portion top, a top teeth portion bottom opposite the top teeth portion top, a top teeth portion left side and a top teeth portion right side opposite the top teeth portion left side.

In another aspect, the bottom teeth engaging portion may include a bottom teeth portion first end, a bottom teeth portion second end opposite the bottom teeth portion first end, a bottom teeth portion length between the bottom teeth portion first end and the bottom teeth portion second end, a bottom teeth portion top, a bottom teeth portion bottom opposite the bottom teeth portion top, a bottom teeth portion left side and a bottom teeth portion right side opposite the bottom teeth portion left side.

In another aspect, the top teeth engaging portion includes a pair of top teeth surrounding members extending upwardly from the top teeth portion top of the top teeth engaging portion.

In another aspect, similarly, the bottom teeth engaging portion includes a pair of bottom teeth surrounding members extending downwardly from the bottom teeth portion bottom of the bottom teeth engaging portion.

In another aspect, the bottom teeth portion length of the bottom teeth engaging portion may be smaller than the top teeth portion length of the top teeth engaging portion.

In another aspect, as such, the pair of bottom teeth surrounding members and the pair of top teeth surrounding members may be staggered, with the pair of bottom teeth surrounding members on the bottom teeth engaging portion set back further than the pair of top teeth surrounding members on the top teeth engaging portion.

In another aspect, due to the staggered configuration of the pair of bottom teeth surrounding members and the pair of top teeth surrounding members, during wear, the lower jaw is moved forward, preventing snoring by maintaining an open airway.

In another aspect, the connecting portion may include a connecting portion first end, a connecting portion second end opposite the connecting portion first end, a connecting portion top, a connecting portion bottom opposite the connecting portion top, a connecting portion left side and a connecting portion right side opposite the connecting portion left side.

In another aspect, the connecting portion may include a biasing member disposed therein for holding the pair of top teeth surrounding members and the pair of bottom teeth surrounding members to the top and bottom teeth of the wearer, respectively, via biasing pressure.

In another aspect, the connecting portion may include an adjustable strap bore through the connecting portion left side through to the connecting portion right side.

In another aspect, the snore prevention clip may further comprise an adjustable strap configured to hold the snore prevention clip on the head of the wearer, preventing choking on the snore prevention clip. This may be particularly useful for back sleepers.

In another aspect, the adjustable strap is configured for insertion through the adjustable strap bore in the connecting portion, connecting the adjustable strap to the snore prevention clip and is subsequently able to attach around the head of the wearer to secure the snore prevention clip to the head of the wearer.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

It should be appreciated that the term "comprising" can also encompass the terms "consisting essentially of" and "consisting of".

Shown throughout the figures, the present invention is directed toward a snore prevention clip. The snore prevention clip provides a minimally obstructive clip that attaches to the teeth of a wearer with the majority of the snore prevention clip being held outside the mouth of the wearer. The snore prevention clip does not dislodge during sleep and comfortably holds the lower jaw forward, keeping the airway of a wearer open and thereby preventing snoring.

Referring initially to FIGS. 1-4, there are shown various views of a snore prevention clip 100, according to one or more embodiments of the present disclosure. As shown here, the snore prevention clip 100 may comprise a top teeth engaging portion 102, a bottom teeth engaging portion 104 and a connecting portion 105 at which the top teeth engaging portion 102 and the bottom teeth engaging portion 104 are joined. In particular, the top teeth engaging portion 102, the bottom teeth engaging portion 104 and the connecting portion 105 may be formed as one unitary piece. The snore prevention clip 100 may be coated in medical grade thermoplastic elastomer material and/or stainless steel material.

Figure 1:
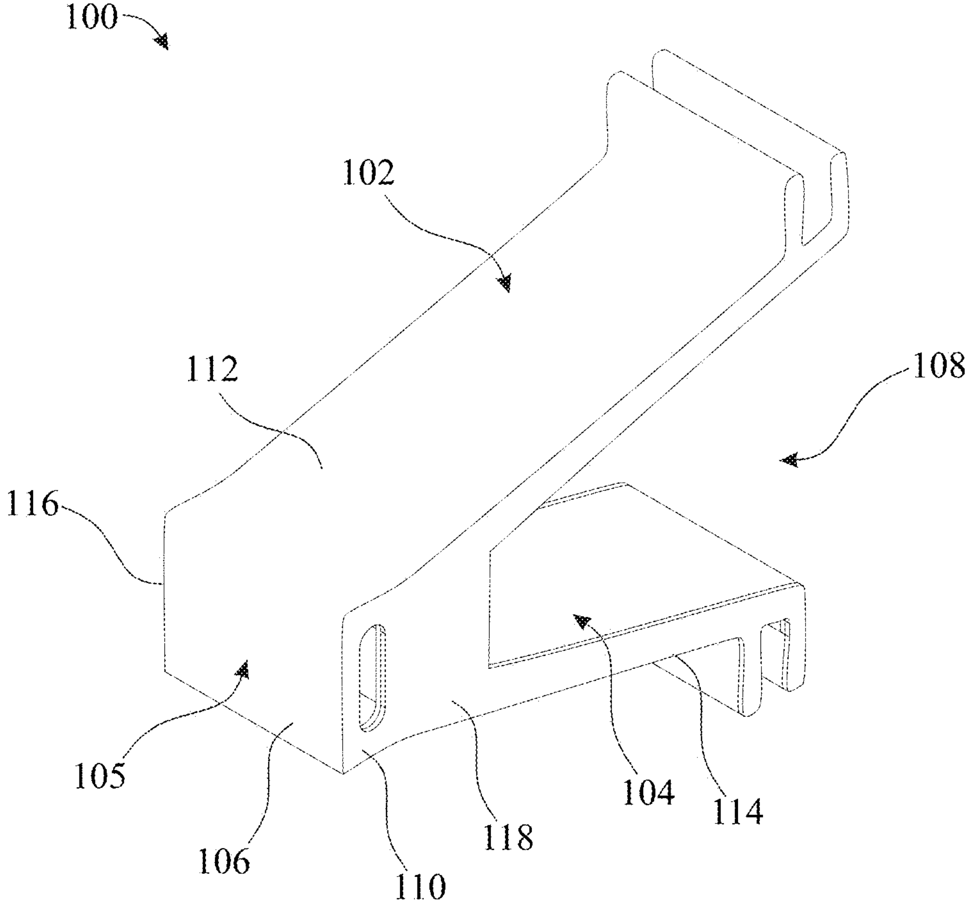
FIG. 1 presents a rear perspective view of a snore prevention clip comprising a top teeth engaging portion, a bottom teeth engaging portion and a connecting portion at which the top teeth engaging portion and the bottom teeth engaging portion are joined, according to one or more embodiments of the present invention.

As demonstrated in FIG. 1, the snore prevention clip 100 may include a snore prevention clip first end 106, a snore prevention clip second end 108 opposite the snore prevention clip first end 106, a snore prevention clip length 110 between the snore prevention clip first end 106 and the snore prevention clip second end 108, a snore prevention clip top 112, a snore prevention clip bottom 114 opposite the snore prevention clip top 112, a snore prevention clip left side 116 and a snore prevention clip right side 118 opposite the snore prevention clip left side 116.

As shown throughout FIGS. 1-4, the top teeth engaging portion 102 and the bottom teeth engaging portion 104 may be formed as a pair of flexible jaws joined together and able to move relative to the connecting portion 105.

The top teeth engaging portion 102 may include a top teeth portion first end 120, a top teeth portion second end 122 opposite the top teeth portion first end 120, a top teeth portion length 123 between the top teeth portion first end 120 and the top teeth portion second end 122, a top teeth portion top 124, a top teeth portion bottom 125 opposite the top teeth portion top 124, a top teeth portion left side 126 and a top teeth portion right side 127 opposite the top teeth portion left side 126. Similarly, the bottom teeth engaging portion 104 may include a bottom teeth portion first end 128, a bottom teeth portion second end 129 opposite the bottom teeth portion first end 128, a bottom teeth portion length 130 between the bottom teeth portion first end 128 and the bottom teeth portion second end 129, a bottom teeth portion top 131, a bottom teeth portion bottom 132 opposite the bottom teeth portion top 131, a bottom teeth portion left side 134 and a bottom teeth portion right side 136 opposite the bottom teeth portion left side 134.

The connecting portion 105 may include a connecting portion first end 154, a connecting portion second end 156 opposite the connecting portion first end 154, a connecting portion top 158, a connecting portion bottom 160 opposite the connecting portion top 158, a connecting portion left side 162 and a connecting portion right side 164 opposite the connecting portion left side 162. As shown here, the top teeth portion length 123 of the top teeth engaging portion 102 and the bottom teeth portion length 130 of the bottom teeth engaging portion 104 may span at least a portion of the snore prevention clip length 110, with the top teeth portion second end 122 and the bottom teeth portion second end 129 terminating at the snore prevention clip second end 108.

As shown throughout these figures, the top teeth engaging portion 102 includes a pair of top teeth surrounding members 138, 140 extending upwardly from the top teeth portion top 124 of the top teeth engaging portion 102. In particular, the pair of top teeth surrounding members 138, 140 includes a first top teeth surrounding member 138 and a second top teeth surrounding member 140 spaced apart such that a top teeth receiving opening 178 is defined between the first top teeth surrounding member 138 and the second top teeth surrounding member 140.

The pair of top teeth surrounding members 138, 140 may each include a top teeth surrounding member inner side 142 and a top teeth surrounding member outer side 144 opposite the top teeth surrounding member inner side 142. As such, the top teeth of the wearer 5 are cradled between the top teeth surrounding member inner side 142 of each of the pair of top teeth surrounding members 138, 140.

Figure 2:
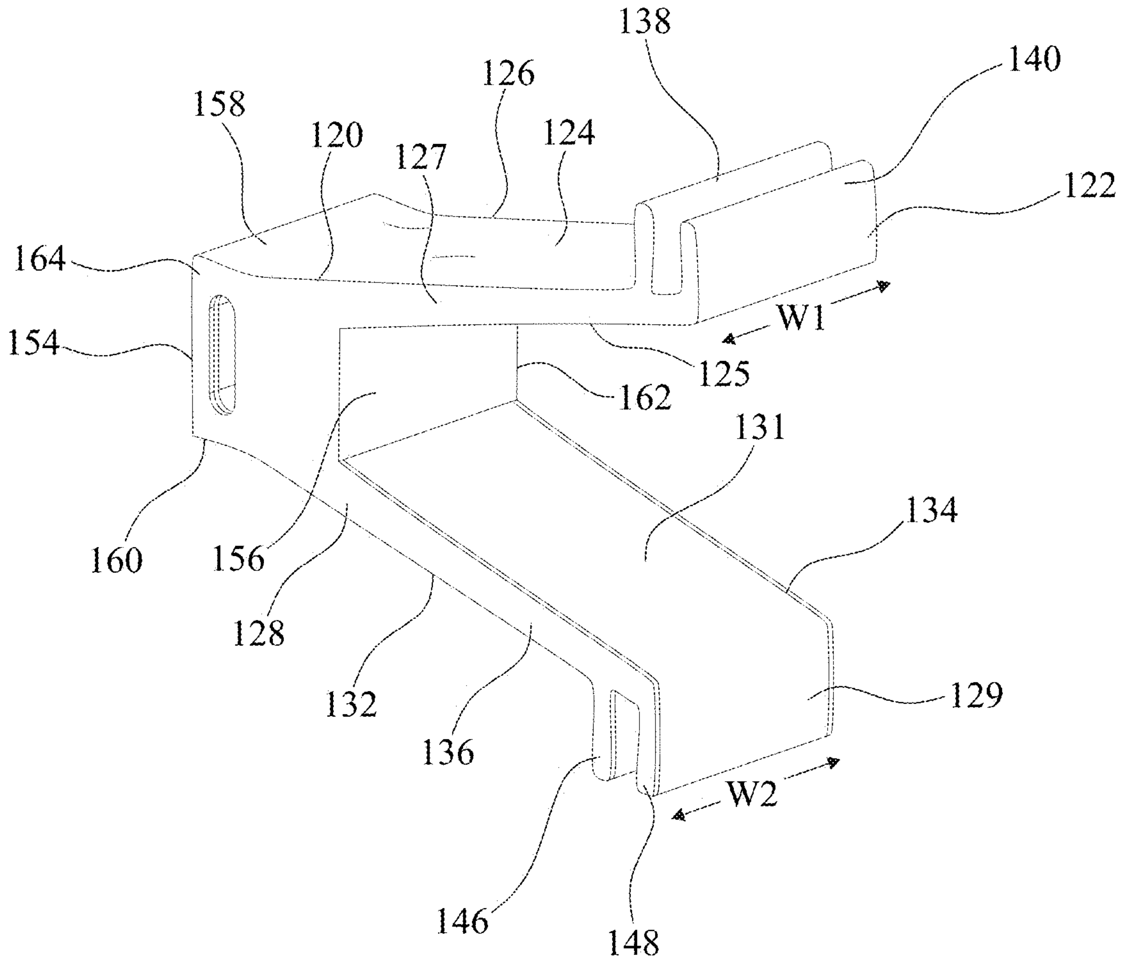
FIG. 2 presents a front perspective view of the snore prevention clip, according to one or more embodiments of the present invention.

As particularly demonstrated in FIG. 2, the pair of top teeth surrounding members 138, 140 and thus, the top teeth receiving opening 178, may include a width W1 equal to, or at least substantially equal to, a combined width of the two front top teeth of the wearer 5, such that the two front top teeth are able to be inserted into the top teeth receiving opening 178 and held between the pair of top teeth surrounding members 138, 140.

Figure 3:
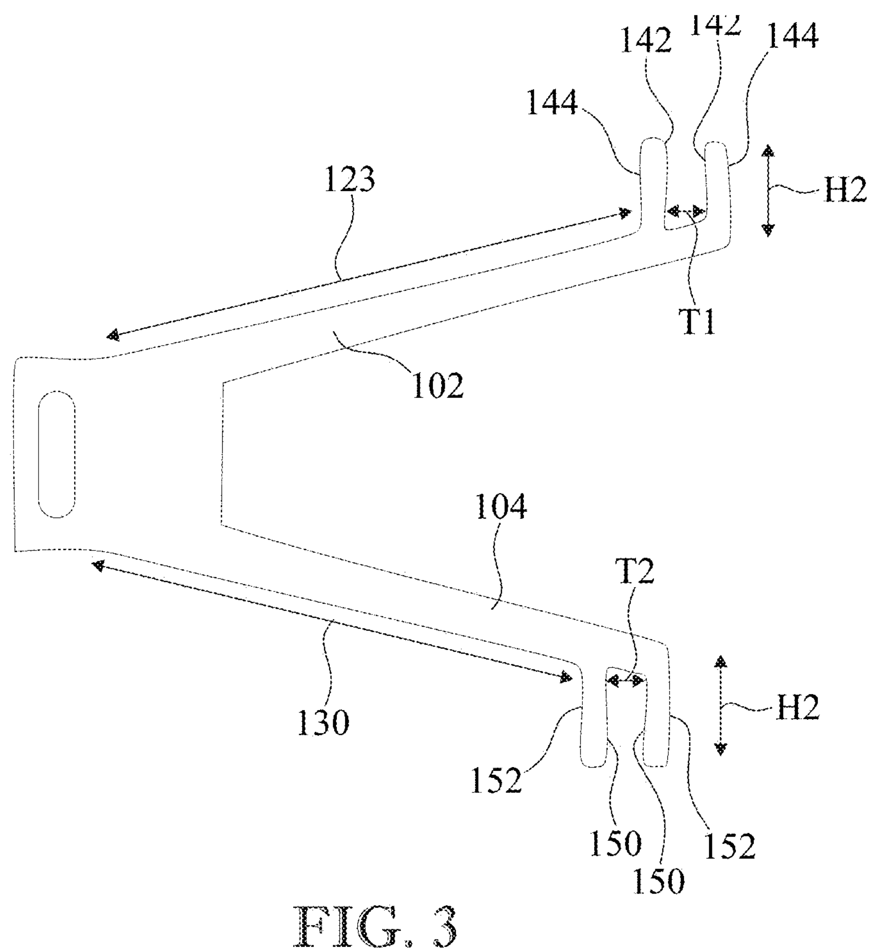
FIG. 3 presents a side view of the snore prevention clip illustrating a pair of top teeth engaging members with a top teeth receiving opening therein and a pair of bottom teeth engaging members with a bottom teeth receiving opening therein, according to one or more embodiments of the present invention.

As particularly demonstrated in FIG. 3, the top teeth receiving opening 178 may include a thickness T1 equal to a thickness of the top teeth of the wearer 5, such that the top teeth are able to be inserted into the top teeth receiving opening 178 and sandwiched in between the pair of top teeth surrounding members 138, 140. Further, the top teeth receiving opening 178 may include a height H1 equal to, or at least substantially equal to, the two front top teeth of the wearer 5.

Similarly, as also shown through, the bottom teeth engaging portion 104 includes a pair of bottom teeth surrounding members 146, 148 extending upwardly from the bottom teeth portion top 131 of the bottom teeth engaging portion 104. In particular, the pair of bottom teeth surrounding members 146, 148 includes a first bottom teeth surrounding member 146 and a second bottom teeth surrounding member 148 spaced apart such that a bottom teeth receiving opening 179 is defined between the first bottom teeth surrounding member 146 and the second bottom teeth surrounding member 148.

The pair of bottom teeth surrounding members 146, 148 may each include a bottom teeth surrounding member inner side 150 and a bottom teeth surrounding member outer side 152 opposite the bottom teeth surrounding member inner side 150. As such, the bottom teeth of the wearer 5 are cradled between the bottom teeth surrounding member inner side 150 of each of the pair of bottom teeth surrounding members 146, 148.

As particularly demonstrated in FIG. 2, the pair of bottom teeth surrounding members 146, 148 and thus, the bottom teeth receiving opening 179, may include a width W2 equal to, or at least substantially equal to, a combined width of the two front bottom teeth of the wearer 5, such that the two front bottom teeth are able to be inserted into the bottom teeth receiving opening 179 and held between the pair of bottom teeth surrounding members 146, 148.

As particularly demonstrated in FIG. 3, the bottom teeth receiving opening 179 may include a thickness T2 equal to a thickness of the bottom teeth of the wearer 5, such that the bottom teeth are able to be inserted into the bottom teeth receiving opening 179 and sandwiched thereinbetween the pair of bottom teeth surrounding members 146, 148. Further, the bottom teeth receiving opening 179 may include a height H2 equal to, or at least substantially equal to, the two front bottom teeth of the wearer 5.

As shown best in FIG. 3, the bottom teeth portion length 130 of the bottom teeth engaging portion 104 may be smaller than the top teeth portion length 123 of the top teeth engaging portion 102. As such, the pair of bottom teeth surrounding members 146, 148 and the pair of top teeth surrounding members 138, 140 may be staggered, with the pair of bottom teeth surrounding members 146, 148 on the bottom teeth engaging portion 104 set back further than the pair of top teeth surrounding members 138, 140 on the top teeth engaging portion 102. Due to the staggered configuration of the pair of bottom teeth surrounding members 146, 148 and the pair of top teeth surrounding members 138, 140, during wear, the lower jaw is moved forward, preventing snoring by maintaining an open airway.

Figure 4:
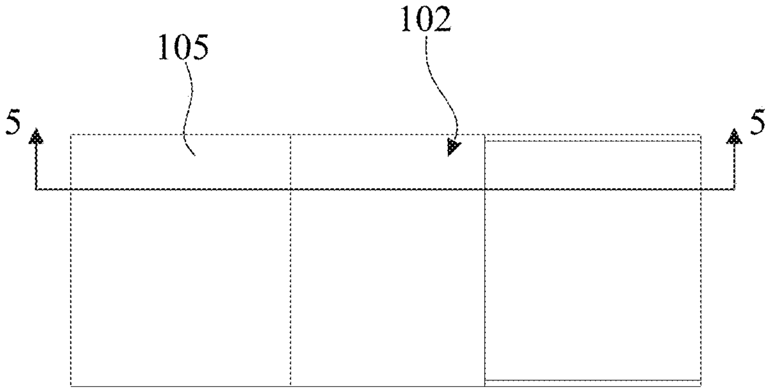
FIG. 4 presents a top view of the snore prevention clip, according to one or more embodiments of the present invention.
Figure 5:
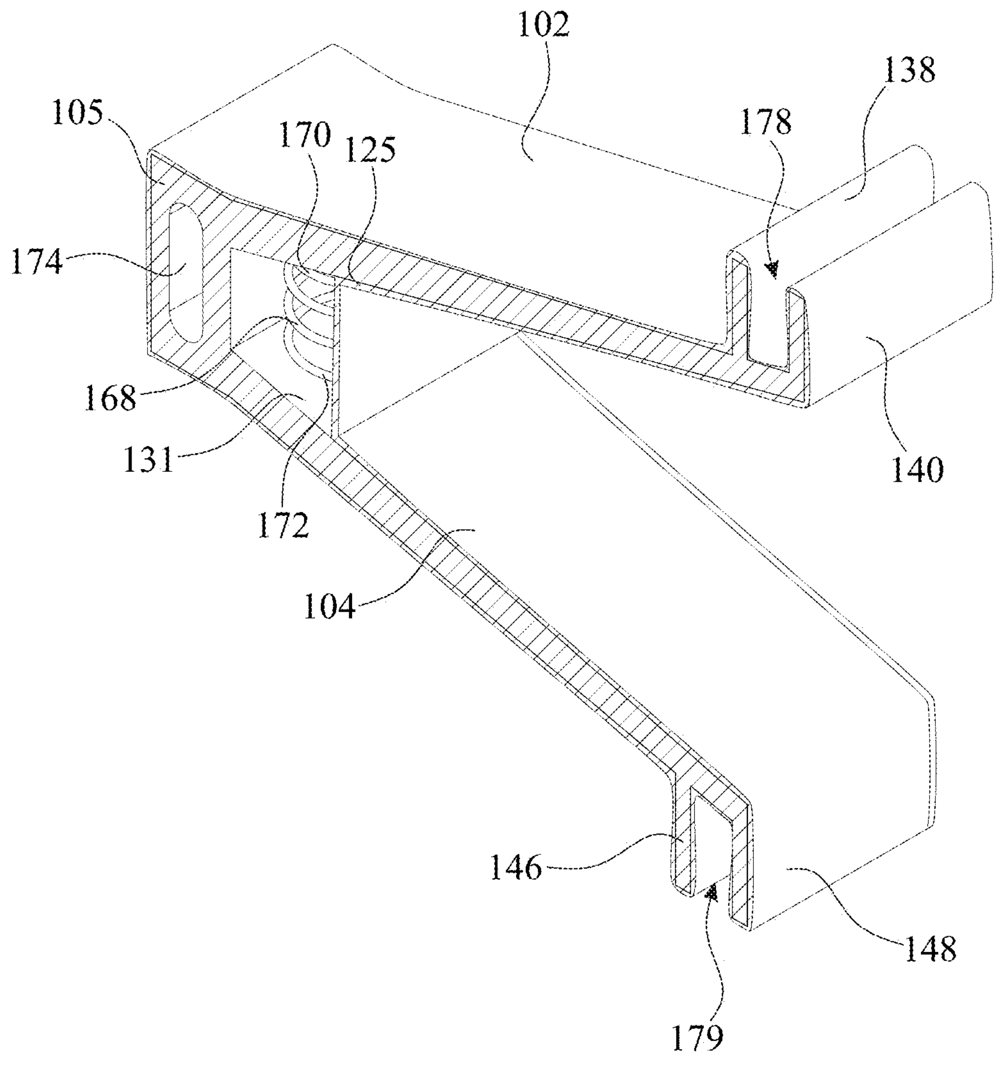
FIG. 5 presents a cross-section view of the snore prevention clip taken from line 5-5 in FIG. 4 and illustrating a spring disposed within the connecting portion, enabling movement and flexing of the top teeth engaging portion and the bottom teeth engaging portion relative to each other, according to one or more embodiments of the present invention.

Referring now also to FIG. 5, which shows a cross-section view of snore prevention clip 100 taken from line 5-5 in FIG. 4, according to one or more embodiments of the present disclosure. As shown here, the connecting portion 105 may include a biasing member disposed therein for holding the pair of top teeth surrounding members 138, 140 and the pair of bottom teeth surrounding members 146, 148 to the top and bottom teeth of the wearer 5, respectively, via biasing pressure. In particular, the biasing member may include a spring 168.

As shown here, the spring 168 may include a spring top side 170 and a spring bottom side 172 opposite the spring top side 170. The spring top side 170 may be attached to the top teeth engaging portion 102 bottom of the top teeth engaging portion 102 at the top teeth engaging portion 102 first end thereof, and similarly, the spring bottom side 172 may be attached to the bottom teeth engaging portion 104 top of the bottom teeth engaging portion 104 at the bottom teeth engaging portion 104 first end thereof. As such, the spring 168 enables movement and flexing of the top teeth engaging portion 102 and the bottom teeth engaging portion 104 relative to each other.

In a neutral position of the spring 168, a distance D (FIG. 6A) between the pair of top teeth surrounding members 138, 140 and the pair of bottom teeth surrounding members 146, 148 is slightly greater than a distance between the top teeth and the bottom of the wearer 5. As such, a squeezing pressure asserted on the top teeth engaging portion 102 and the bottom teeth engaging portion 104 to bring them together compresses the spring 168 into a biasing position such that once the squeezing pressure is removed, the pressure built up in the spring 168 urges the top teeth engaging portion 102 and the bottom teeth engaging portion 104 apart, to return back into the neutral position.

Accordingly, the squeezing pressure is applied when the wearer 5 places the snore prevention clip 100 into their mouth and aligns the pair of top teeth surrounding members 138, 140 with their top teeth and the pair of bottom teeth surrounding members 146, 148 with their bottom teeth. Once aligned, the wearer 5 stops squeezing, which urges the air of top teeth surrounding members 138, 140 and the pair of bottom teeth surrounding members 146, 148 against the top teeth and the bottom teeth, respectively, thereby securing the snore prevention clip 100 to the top and bottom teeth via pressure as, due to the distance between the pair of top teeth surrounding members 138, 140 and the bottom teeth surrounding members 146, 148 being slightly greater than the distance between the top teeth and the bottom of the wearer 5, the spring 168 is unable to return to its neural position.

Figure 6A:
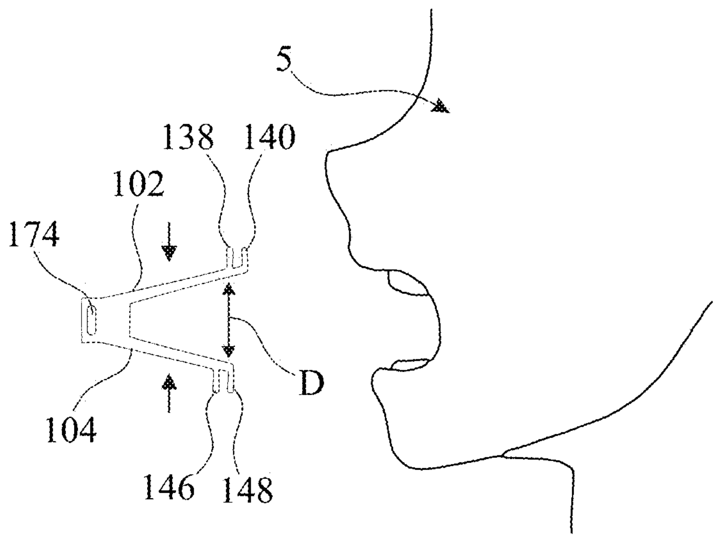
FIG. 6A presents a side view of the snore prevention clip being inserted into the mouth of a wearer, according to one or more embodiments of the present invention.
Figure 6B:
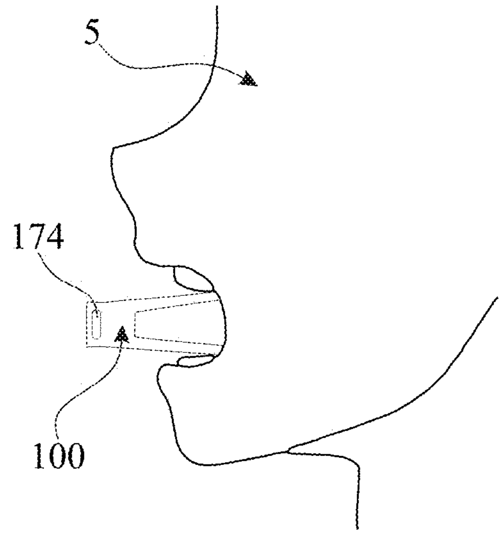
FIG. 6B presents a side view of the snore prevention clip having been inserted into the mouth of the wearer and in an in use position, according to one or more embodiments of the present invention.
Figure 7:
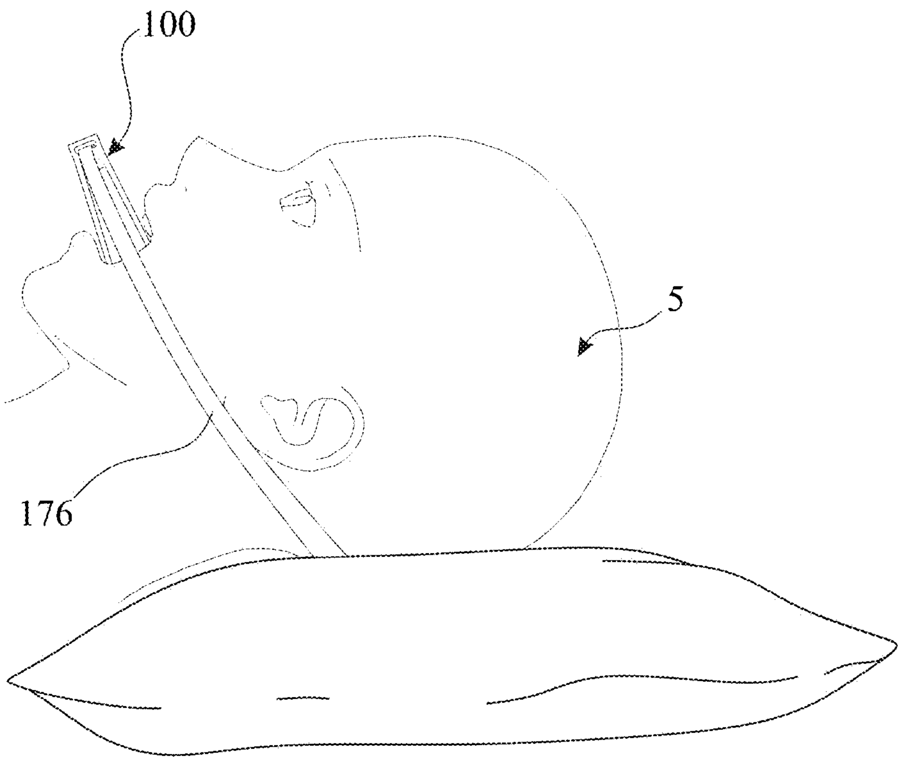
FIG. 7 presents a side view of the snore prevention clip with an adjustable strap being worn by a back sleeping wearer, according to one or more embodiments of the present invention.

Referring now also to FIGS. 6A-7, showing various views of the snore prevention clip in use, according to one or more embodiments of the present disclosure. As demonstrated in FIGS. 6A-6B, in use, the wearer 5 applies a squeezing pressure to the top teeth engaging portion 102 and the bottom teeth engaging portion 104 to bring them together and move the spring 168 into the biasing position. The wearer 5 aligns the pair of top teeth surrounding members 138, 140 with their top teeth, inserting their top teeth into the top teeth receiving opening 178, and aligns the pair of bottom teeth surrounding members 146, 148 with their bottom teeth, inserting their bottom teeth into the bottom teeth receiving opening 179. The wearer 5 then removes the squeezing pressure, which urges the top teeth engaging portion 102 and the bottom teeth engaging portion 104 against the top and bottom teeth, respectively, as the spring 168 tries to return to its neutral position. The spring 168 pressure is able to secure the snore prevention clip 100 to the top and bottom teeth if the wearer 5 is a side or stomach sleeper.

As demonstrated in FIG. 7, in some embodiments, the snore prevention clip 100 may further comprise an adjustable strap 176 configured to hold the snore prevention clip 100 on the head of the wearer 5, preventing choking on the snore prevention clip 100. This may be particularly useful for back sleepers. As such, as shown in FIGS. 5-6B the connecting portion 105 may include an adjustable strap bore 174 through the connecting portion left side 162 through to the connecting portion right side 164.

The adjustable strap 176 is configured for insertion through the adjustable strap bore 174 in the connecting portion 105, connecting the adjustable strap 176 to the snore prevention clip 100 and is subsequently able to attach around the head of the wearer 5 to secure the snore prevention clip 100 to the head of the wearer 5. As such, if the wearer 5 is a back sleeper, the wearer 5 may insert the adjustable strap 176 through the adjustable strap bore 174 in the connecting portion 105 of the snore prevention clip 100 and fasten the adjustable strap 176 to their head. As such, the snore prevention clip 100 is secured to prevent inadvertent choking on the snore prevention clip 100.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A snore prevention clip, said snore prevention clip comprising:
- a top teeth engaging portion;
- a bottom teeth engaging portion;
- a connecting portion at which the top teeth engaging portion and the bottom teeth engaging portion are joined; and
- wherein the connecting portion is positioned outside of a mouth when the top teeth engaging portion and bottom teeth engaging portion are engaged with a wearer's top and bottom teeth respectively.

2. The snore prevention clip of claim 1, wherein the top teeth engaging portion includes a top teeth portion first end, a top teeth portion second end opposite the top teeth portion first end, a top teeth portion length between the top teeth portion first end and the top teeth portion second end, a top teeth portion top, a top teeth portion bottom opposite the top teeth portion top, a top teeth portion left side and a top teeth portion right side opposite the top teeth portion left side.

3. The snore prevention clip of claim 2, wherein the bottom teeth engaging portion includes a bottom teeth portion first end, a bottom teeth portion second end opposite the bottom teeth portion first end, a bottom teeth portion length between the bottom teeth portion first end and the bottom teeth portion second end, a bottom teeth portion top, a bottom teeth portion bottom opposite the bottom teeth portion top, a bottom teeth portion left side and a bottom teeth portion right side opposite the bottom teeth portion left side.

4. The snore prevention clip of claim 3, wherein the top teeth engaging portion includes a pair of top teeth surrounding members extending upwardly from the top teeth portion top of the top teeth engaging portion.

5. The snore prevention clip of claim 3, wherein the bottom teeth portion length of the bottom teeth engaging portion is smaller than the top teeth portion length of the top teeth engaging portion.

6. The snore prevention clip of claim 2, wherein the pair of bottom teeth surrounding members and the pair of top teeth surrounding members are staggered with respect to each other.

7. The snore prevention clip of claim 6, wherein the connecting portion includes a connecting portion first end, a connecting portion second end opposite the connecting portion first end, a connecting portion top, a connecting portion bottom opposite the connecting portion top, a connecting portion left side and a connecting portion right side opposite the connecting portion left side.

8. The snore prevention clip of claim 7, wherein the connecting portion includes a biasing member disposed therein configured to hold the pair of top teeth surrounding members and the pair of bottom teeth surrounding members to the top and bottom teeth of the wearer, respectively, via a biasing pressure.

9. The snore prevention clip of claim 8, wherein the connecting portion includes an adjustable strap bore through the connecting portion left side through to the connecting portion right side.

10. The snore prevention clip of claim 9, wherein the snore prevention clip further comprises an adjustable strap configured to hold the snore prevention clip on a head of the wearer.

11. The snore prevention clip of claim 10, wherein the adjustable strap is configured for insertion through the adjustable strap bore in the connecting portion.

12. The snore prevention clip of claim 4, the bottom teeth engaging portion includes a pair of bottom teeth surrounding members extending downwardly from the bottom teeth portion bottom of the bottom teeth engaging portion.

13. The snore prevention clip of claim 1, wherein the top teeth engaging portion, the bottom teeth engaging portion and the connecting portion are formed as one unitary piece.

14. The snore prevention clip of claim 1, wherein the snore prevention clip includes a snore prevention clip first end, a snore prevention clip second end opposite the snore prevention clip first end, a snore prevention length between the snore prevention clip first end and the snore prevention clip second end, a snore prevention clip top, a snore prevention clip bottom opposite the snore prevention clip top, a snore prevention clip left side and a snore prevention clip right side opposite the snore prevention clip left side.

15. The snore prevention clip of claim 1, wherein the top teeth engaging portion and the bottom teeth engaging portion are formed as a pair of flexible jaws joined together by, and able to move relative to the connecting portion.

* * * * *